United States Patent [19]

Betka

[11] 4,013,187
[45] Mar. 22, 1977

[54] HANGER CONSTRUCTION FOR SEMIRIGID PLASTIC CONTAINER

[75] Inventor: Harold Anthony Betka, Waukegan, Ill.

[73] Assignee: Abbott Laboratories, Chicago, Ill.

[22] Filed: May 28, 1974

[21] Appl. No.: 473,609

[52] U.S. Cl. .......................................... 215/100 A
[51] Int. Cl.² ........................................ B65D 23/00
[58] Field of Search ............... 215/100 A, 100 R; 248/359, 360; 222/180, 181; 206/806

[56] References Cited
UNITED STATES PATENTS

| | | | |
|---|---|---|---|
| 2,304,547 | 12/1942 | Cutter | 248/359 |
| 3,387,732 | 6/1968 | Jellies | 215/100 A |
| 3,581,928 | 6/1971 | Amand | 215/100 A |

*Primary Examiner*—Donald F. Norton
*Attorney, Agent, or Firm*—Aaron L. Hardt; Robert L. Niblack

[57] ABSTRACT

A semirigid plastic container having a hanger removably mounted on an elongated, inverted T-shaped rib integral with and depending from its base. Preferably, the T-shaped rib has a transverse lug disposed thereon adapted for locking the hanger in place.

7 Claims, 4 Drawing Figures

HANGER CONSTRUCTION FOR SEMIRIGID PLASTIC CONTAINER

BACKGROUND OF THE INVENTION

This invention relates to a semirigid plastic container and, more particularly, to a hanger construction on the base of such a container.

Parenteral liquid containers usually have some means at their bases for hanging them mouth downwardly when dispensing liquid to a patient. The conventional hanger for a glass bottle is a metal band secured in a groove in the bottle and a wire bail connected to that band. With the advent of plastic bottles as containers for parenteral liquids, it has been proposed to integrally form a hanger tab with the bottom wall of the plastic container as in U.S. Pat. No. 3,208,710. This hanging tab was integrally joined to a flexible web so that it could fold into a recess in the bottom wall of the container disclosed in U.S. Pat. No. 3,215,299 and was provided with a means of retention within such a recess in U.S. Pat. No. 3,387,732.

A primary consideration in the usefulness of parenteral liquid containers is that they be substantially clear, lucid or transparent to allow for visual inspection of the purity of their contents. A semirigid plastic container having substantially the lucidity of clear glass can be made according to the process taught in U.S. Pat. No. 3,228,317 entitled "Molecularly Oriented Bottle" and granted to Fred E. Wiley on Nov. 29, 1966. Unfortunately, it is extremely difficult to mold an integral hanger to the otherwise satisfactory and preferred container made by the process of the U.S. Pat. No. 3,288,317 patent.

Further, a semirigid plastic container having an intergral hanger molded thereon is difficult to use if that hanger is broken or removed from the container for any reason, since normally there is no means on the container by which another hanger can be attached.

SUMMARY OF THE INVENTION

Therefore, the primary object of the present invention is to provide a semirigid plastic container having a removably mounted hanger means connected to its base. This object is accomplished in the present invention by the provision of a semirigid plastic container comprising a body having an integral base with an elongated, inverted T-shaped rib formed integral with and depending from that base. A loop integrally joined to an elongated, substantially C-shaped bar complementary to the T-shaped rib is slid onto the rib to provide a hanger for the container. Preferably, the T-shaped rib has a transverse lug disposed thereon adapted for locking the hanger in place.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
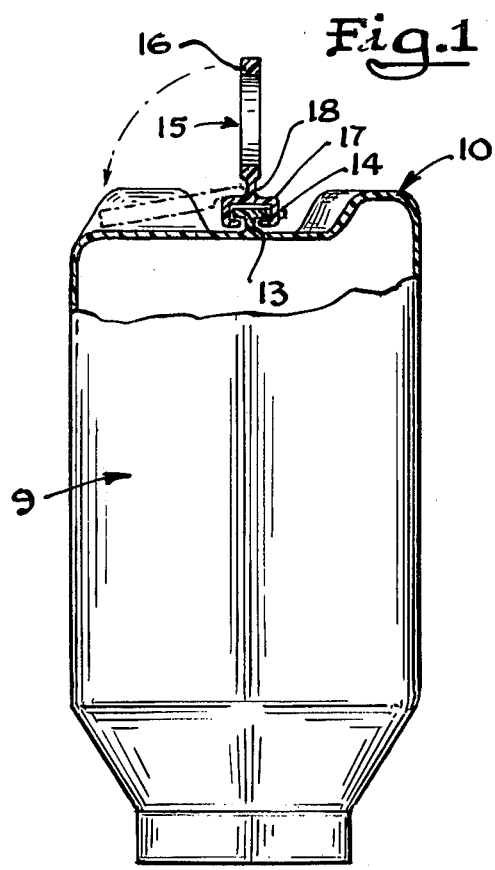
FIG. 1 is a side view, partially in section, of one semirigid plastic container embodying the present invention.

Referring now to the drawing, there is generally shown in FIG. 1 a semirigid plastic container 9 having an integral base 10. Container 9 can be extruded, thermoformed or blowmolded from any suitable thermoplastic polymer. Preferably, container 9 is made of a crystallizable polymer which can be molecularly oriented on stretching at carefully controlled temperatures. As disclosed in the above-cited U.S. Pat. No. 3,288,317, substantially transparent containers can be made from molecularly oriented polymers such as polystyrene, polyvinylchloride, nylon, and mono-1-olefins containing up to eight carbon atoms; particularly those olefins of relatively high degree of crystallinity, polyethylene, polypropylene or a mixture thereof.

Figure 2:
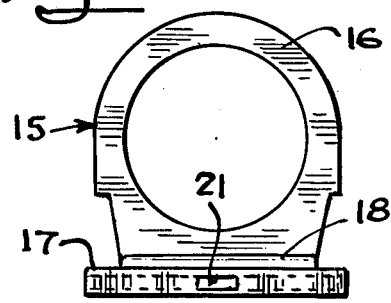
FIG. 2 is a front view of one integral hanger contemplated by the present invention.
Figure 3:
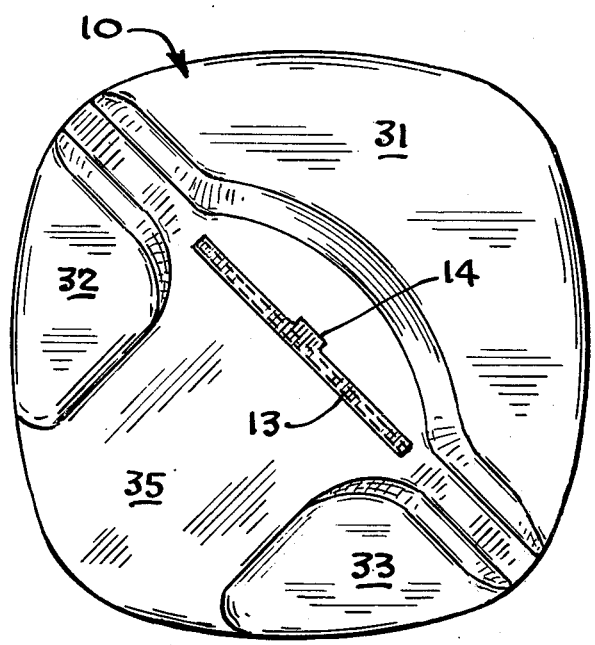
FIG. 3 is a bottom view of another semirigid plastic container embodying the present invention and showing the attachment thereto of the T-shaped bar in a recessed portion of its base.

Molded integral with and depending from base 10 is an elongated, inverted, substantially T-shaped rib 13. As shown in FIG. 3, T-shaped rib 13 preferably has a transverse lug 14 disposed thereon. Although it is not necessary that rib 13 have such a projection, lug 14 provides additional stability for the integral hanger 15 that is removably mounted thereon. As shown in FIGS. 1 and 2, loop 16 is integrally joined to an elongated, substantially C-shaped bar 17 that is complementary to T-shaped rib 13. Hanger 15 can be made of any material desired, although plastic is preferred. Further, loop 16 is preferably joined to C-shaped bar 17 by a flexible web 18. When integral hanger 15 is used with the preferred T-shaped rib 13 having transverse lug 14, hanger 15 is further characterized by an aperture 21 that is complementary to lug 14.

Accordingly, when hanger 15 is slid onto T-shaped rib 13, the semirigid plastic container 9 is thereby provided with a means by which it can be hung. In the preferred embodiment of T-shaped rib 13 having transverse lug 14, hanger 15 is slid onto rib 13 until lug 14 protrudes through aperture 21 and thereby securely locks hanger 15 onto rib 13. However, if necessary, hanger 15 can be removed from rib 13 and replaced by another hanger.

Figure 4:
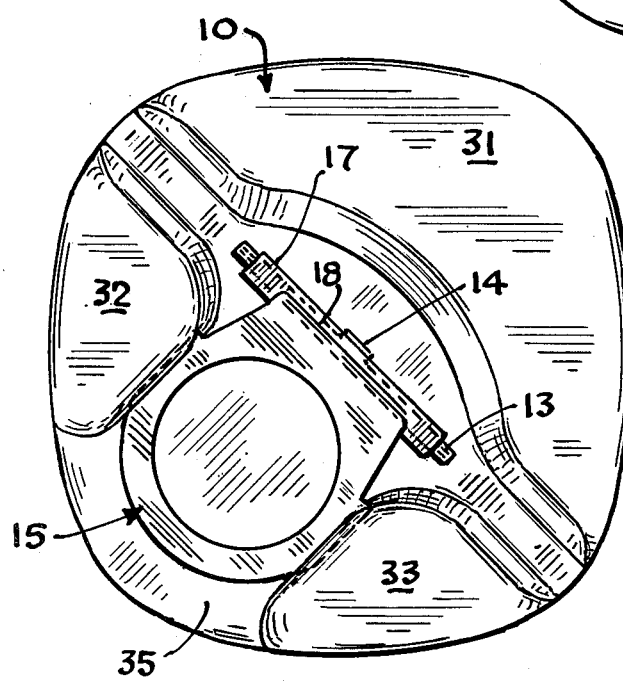
FIG. 4 is a bottom view of the container shown in FIG. 3 and having the integral hanger shown in FIG. 2 attached thereon.

As shown in FIGS. 3 and 4, in one preferred embodiment of the semirigid container 9 of the present invention, integral base 10 can have protuberant base sections 31, 32 and 33 that are adapted to rest on a flat surface and an indented base wall 35 spaced from the protuberant base sections 31, 32 and 33 to form a recess in the base 10. Further, either or both of the protuberant base sections 32 and 33 can have undercut wall sections to form at least one retention groove therein. Thus, when loop 16 and C-shaped bar 17 are joined by a flexible web 18, integral hanger 15 can be retained within recess 35 by means of the groove(s) formed in base protuberances 32 and/or 33. In such an instance, it will be readily apparent that recess 35 will be deep enough so that hanger 15 will not interfere with the adaptation of sections 31, 32 and 33 to a flat surface.

Having now described the invention in specific detail and exemplified the manner in which it may be carried into practice, it will be readily apparent to those skilled in the art, that innumerable variations, applications, modifications, and extensions of the basic principles involved, may be made without departing from its sphere or scope.

That which I claim is:

1. In a semirigid plastic container comprising a body having an integral base, the improvement which comprises the combination of:

an elongated, inverted, substantially T-shaped rib integral with and depending from said base; and a loop integrally joined to an elongated, substantially C-shaped bar complementary to and removably slid onto said T-shaped rib, whereby said loop provides a hanger for said container.

2. The container defined in claim 1 wherein said loop is flexibly joined to said C-shaped bar.

3. The container defined in claim 2 wherein said integral base includes protuberant base sections adapted to rest on a flat surface and an indented base wall spaced from said base sections to form a recess, at least one of said protuberant base sections having an undercut wall section forming a groove wherein said loop can be removably retained.

4. The container defined in claim 1 wherein said loop and C-shaped bar are made of plastic.

5. The container defined in claim 1 wherein said body and integral are formed of a molecularly oriented plastic.

6. A plastic container having an integral base, an elongated, inverted, substantially T-shaped rib integral with and depending from said base, and a loop integrally joined to an elongated, substantially C-shaped bar complementary to and slidably affixed onto said T-shaped rib.

7. A plastic container having an integral base, an elongated, inverted, substantially T-shaped rib integral with and depending from said base, and a loop integrally joined to an elongated, substantially C-shaped bar complementary to and slidably affixed onto said T-shaped rib, said integral base including protuberant base sections adapted to rest on a flat surface and a recess between said sections, at least one of said sections having an undercut wallsection forming a groove for removably retaining said loop.

* * * * *